US010751873B2

(12) United States Patent
Wang et al.

(10) Patent No.: US 10,751,873 B2
(45) Date of Patent: Aug. 25, 2020

(54) ROBOTIC ARM

(71) Applicant: HIWIN TECHNOLOGIES CORP., Taichung (TW)

(72) Inventors: Ren-Jeng Wang, Taichung (TW); Cheng-Chin Chen, Taichung (TW); Yu-Lin Chu, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 149 days.

(21) Appl. No.: 16/188,858

(22) Filed: Nov. 13, 2018

(65) Prior Publication Data
US 2020/0147790 A1 May 14, 2020

(51) Int. Cl.
| B25J 9/12 | (2006.01) |
| B25J 9/10 | (2006.01) |
| B25J 9/04 | (2006.01) |
| A61B 34/30 | (2016.01) |

(52) U.S. Cl.
CPC ............. B25J 9/1065 (2013.01); B25J 9/042 (2013.01); B25J 9/12 (2013.01); *A61B 34/30* (2016.02)

(58) Field of Classification Search
CPC ............. B25J 9/1065; B25J 9/042; B25J 9/12
See application file for complete search history.

(56) References Cited

U.S. PATENT DOCUMENTS

| 4,762,016 A * | 8/1988 | Stoughton | B25J 9/04 |
| | | | 414/680 |
| 5,222,409 A * | 6/1993 | Dalakian | B25J 9/046 |
| | | | 414/733 |
| 6,047,610 A * | 4/2000 | Stocco | B25J 17/0266 |
| | | | 74/479.01 |
| 6,339,969 B1 * | 1/2002 | Salcudean | B25J 9/106 |
| | | | 74/490.01 |
| 7,331,750 B2 * | 2/2008 | Merz | B25J 9/104 |
| | | | 414/735 |
| 2004/0211284 A1 * | 10/2004 | Roy | B23Q 1/5456 |
| | | | 74/490.01 |
| 2010/0225209 A1 * | 9/2010 | Goldberg | A61B 34/37 |
| | | | 312/209 |

(Continued)

FOREIGN PATENT DOCUMENTS

| CN | 204976631 U | 1/2016 |
| DE | 3038419 A1 | 4/1981 |

(Continued)

*Primary Examiner* — David M Fenstermacher
(74) *Attorney, Agent, or Firm* — Muncy, Geissler, Olds & Lowe, P.C.

(57) ABSTRACT

A robotic arm includes a first driving source and a second driving source mounted on a base frame, a first transmission link driven by the first driving source to turn around a first axis, a second transmission link driven by the second driving source to turn around a second axis that is parallel to the first axis, a third transmission link pivoted to the first transmission link, a first driven link pivoted to the second transmission link, a second driven link pivotally coupled between the first driven link and the base frame, a third driven link pivotally connected with the first and second driven link, and a fourth driven link pivotally coupled between the third driven link and the third transmission link. Thus, the robotic arm of the invention has a compact size and can achieve multi-degree of freedom motion.

6 Claims, 9 Drawing Sheets

(56) References Cited

U.S. PATENT DOCUMENTS

2012/0132018 A1* 5/2012 Tang ..................... A61B 34/70
                                                                                  74/29

FOREIGN PATENT DOCUMENTS

| DE | 102010023788 A1 | 12/2011 |
| DE | 10235191 B4 | 2/2012 |
| DE | 102015102014 A1 | 3/2016 |
| DE | 102014116103 A1 | 5/2016 |
| JP | H02-4788 U | 1/1990 |
| JP | H02-279289 A | 11/1990 |
| JP | 2003-39352 A | 2/2003 |

* cited by examiner

ROBOTIC ARM

BACKGROUND OF THE INVENTION

1. Field of the Invention

The present invention relates to robotic arm technology and more particularly, to a robotic arm, which has a compact size and can achieve multi-degree of freedom motion.

2. Description of the Related Art

The robotic arm is now widely used in a variety of surgical procedures. With the aid of a robotic arm, many surgical-related treatments (such as the judgment of the location of the lesion or the control of the depth of the incision) can be accurately grasped by the surgeon, thereby greatly reducing risk of any potential medical problems caused by human error. However, the current robotic arms have the problem of large volume. When using a robotic arm, it requires a large space.

SUMMARY OF THE INVENTION

The present invention has been accomplished under the circumstances in view. It is the main object of the present invention to provide a robotic arm, which has a compact size and can achieve multi-degree of freedom motion.

To achieve this and other objects of the present invention, a robotic arm comprises a base frame, a drive module, a transmission linkage and a driven link set. The drive module comprises a first driving source and a second driving source. The first driving source and the second driving source are mounted on the base frame. The transmission linkage comprises a first transmission link, a second transmission link and a third transmission link. The first transmission link has a bottom end thereof connected to the first driving source such that the first transmission link can be driven by the first driving source to turn around a first axis. The second transmission link has a front end thereof connected to the second driving source such that the second transmission link can be driven by the second driving source to turn around a second axis that is parallel to the first axis. The third transmission link has a rear end thereof pivotally connected to an opposing top end of the first transmission link. The driven link set comprises a first driven link, a second driven link, a third driven link and a fourth driven link. The first driven link has a bottom end thereof pivotally connected to the rear end of the second transmission link, and an opposing top end thereof pivotally connected to a rear end of the second driven link. The second driven link has an opposing front end thereof pivotally connected to the base frame such that the first driven link can be driven by the second transmission link to turn the second driven link around the first axis. The third driven link has a bottom end thereof pivotally connected to the top end of the first driven link and the rear end of the second driven link, and an opposing top end thereof pivotally connected to a rear end of a fourth driven link. The fourth driven link has an opposing front end thereof connected to the rear end of the third transmission link such that the third driven link on the one hand can be driven by the first and second driven link, and on the other hand can be driven by the fourth driven link.

It can be seen from the above that the robotic arm of the present invention can improve the bulky and cumbersome problems of the prior art and can achieve the effect of compactness and multi-degree of freedom motion and is quite suitable for application in industrial/medical related fields.

Preferably, the first driving source and the second driving source are located on the same side, so that large-volume components can be concentrated to effectively achieve the purpose of volumetric compactness.

Preferably, the second driven link is parallel to the fourth driven link, the length of the second transmission link is greater than the length of the second driven link, and the length of the second driven link is equal to the length of the fourth driven link. The relationship of the second transmission link, the second driven link and the fourth driven link allows the range of motion of the third transmission link to be amplified relative to the second transmission link to meet the required working range.

Other advantages and features of the present invention will be fully understood by reference to the following specification in conjunction with the accompanying drawings, in which like reference signs denote like components of structure.

DETAILED DESCRIPTION OF THE INVENTION

Figure 1:
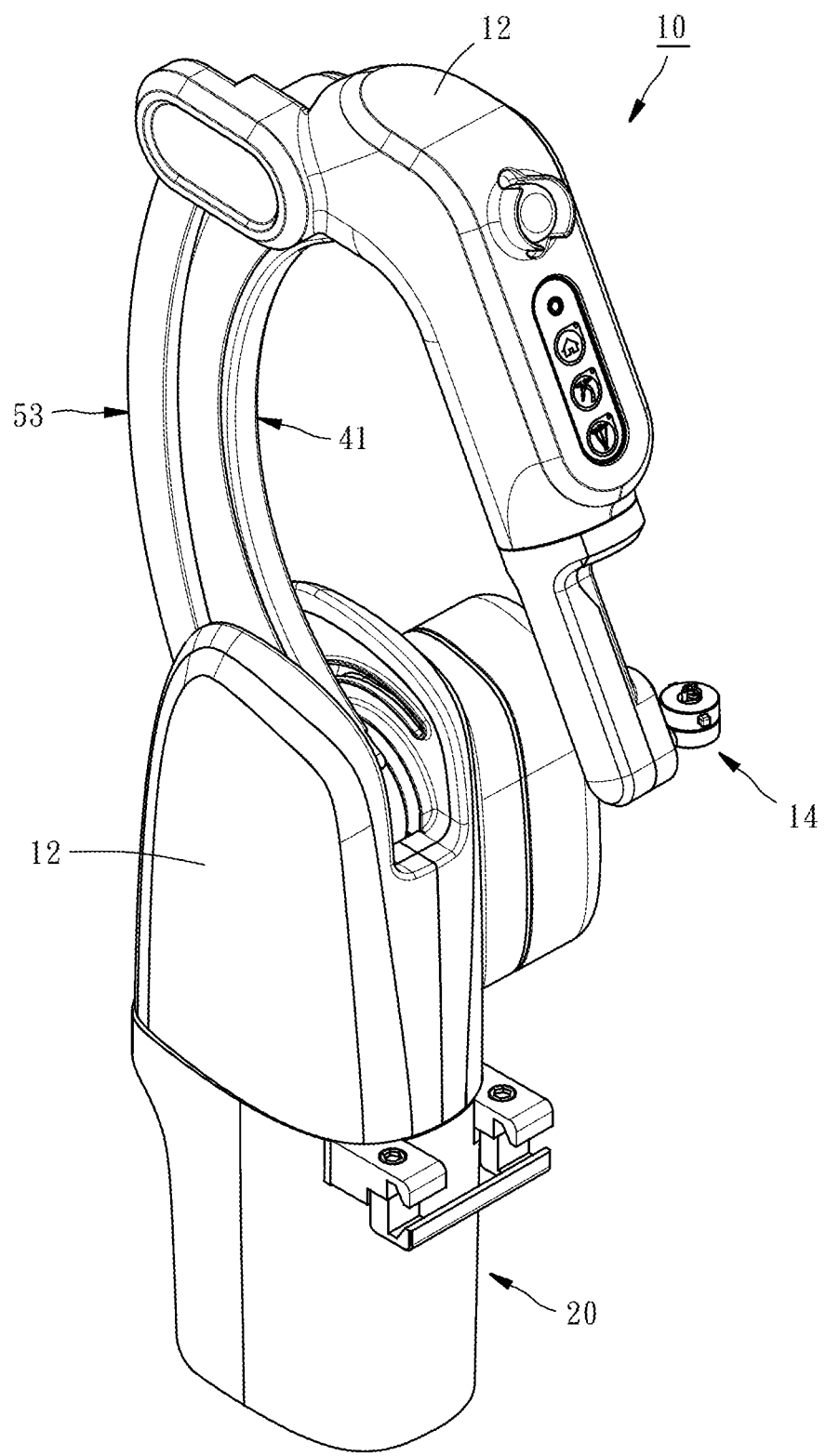
FIG. 1 is an oblique top elevational view of a robotic arm in accordance with a first embodiment of the present invention.

The applicant first explains here, in the embodiments and drawings which will be described below, the same reference numerals denote the same or similar elements or structural features thereof. The technical content and features of the present invention will be described in detail below by way of a number of preferred embodiments as illustrated in the accompanying drawings. The directional expressions such as "top", "bottom", "front" and "back" mentioned in the contents of this description are merely illustrative terms used in the normal direction of use and are not intended to limit the scope of claims.

Figure 2:
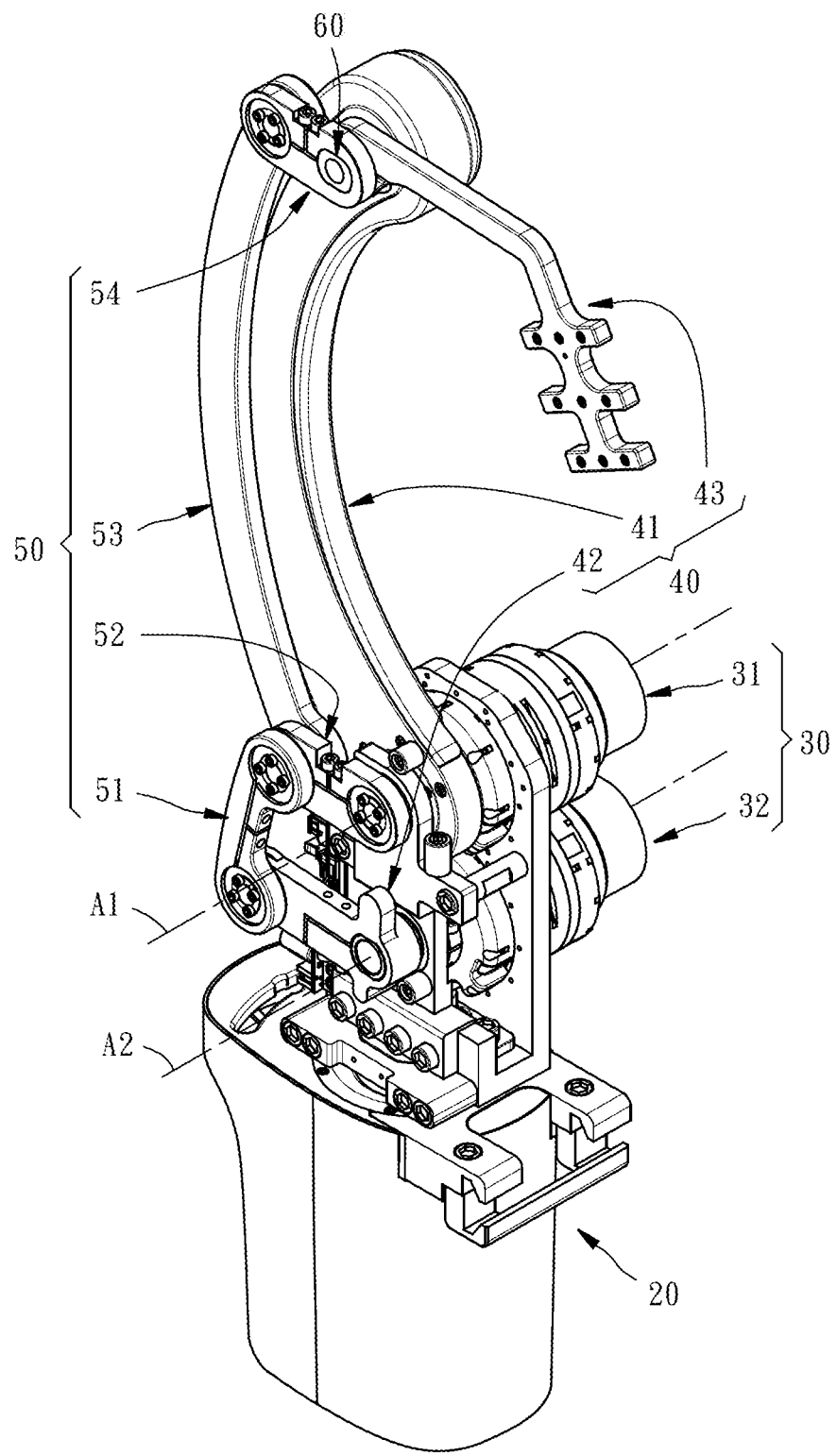
FIG. 2 is an oblique top elevational view of the robotic arm shown in FIG. 1 after removal of the outer casing.
Figure 3:
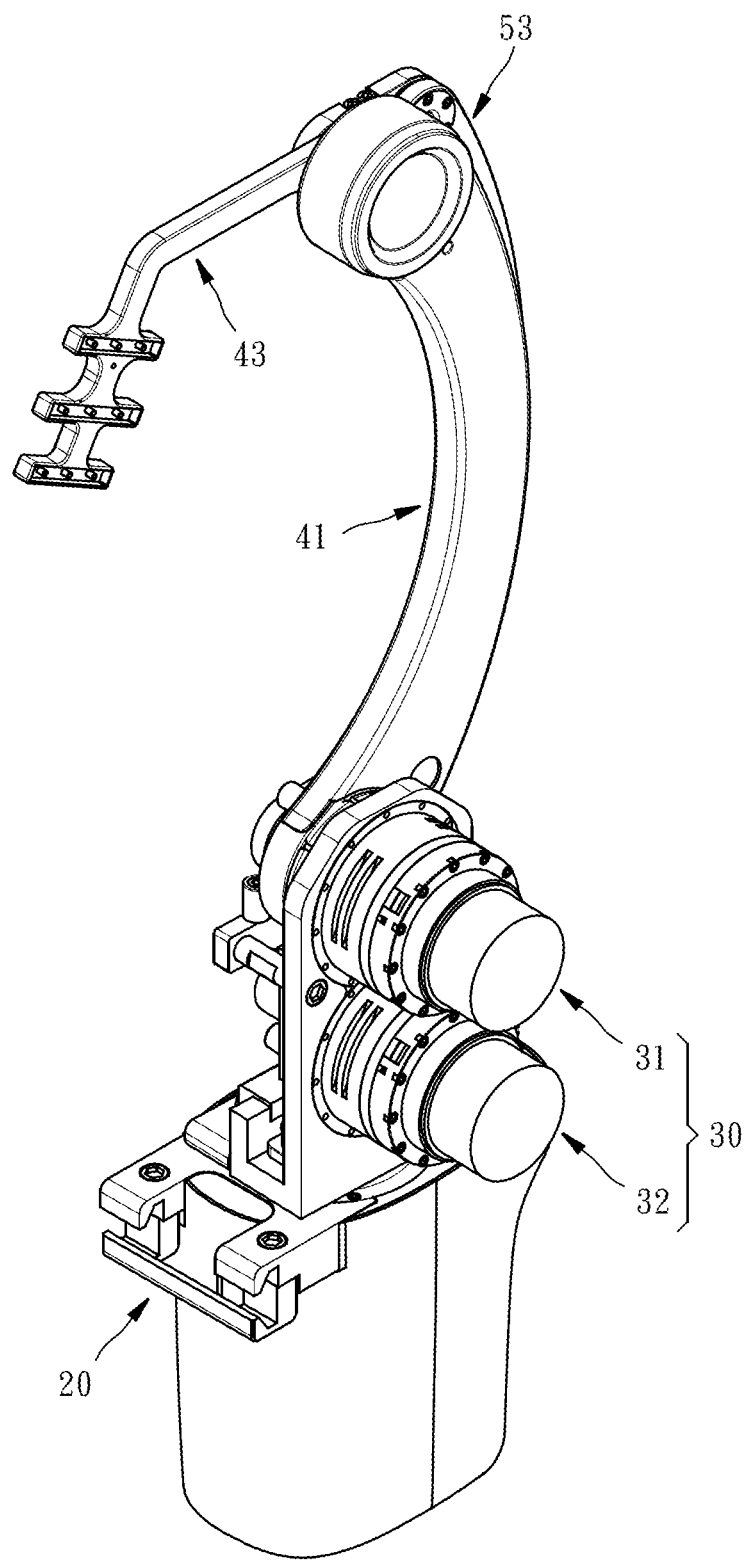
FIG. 3 corresponds to FIG. 2 when viewed from another angle.

Referring to FIG. 1, an oblique top elevation of a robotic arm 10 in accordance with a first embodiment of the present invention is shown. FIGS. 2 and 3 show the aspect of the robotic arm 10 after the outer casing 12 is removed. As illustrated, the robotic arm 10 comprises a base frame 20, a drive module 30, a transmission linkage 40, and a driven link set 50.

The drive module 30 comprises a first driving source 31 (here, a motor is taken as an example) and a second driving source 32 (here, a motor is taken as an example). The first driving source 31 and the second driving source 32 are arranged in parallel at different elevations and on the same side of the base frame 20.

Figure 4:
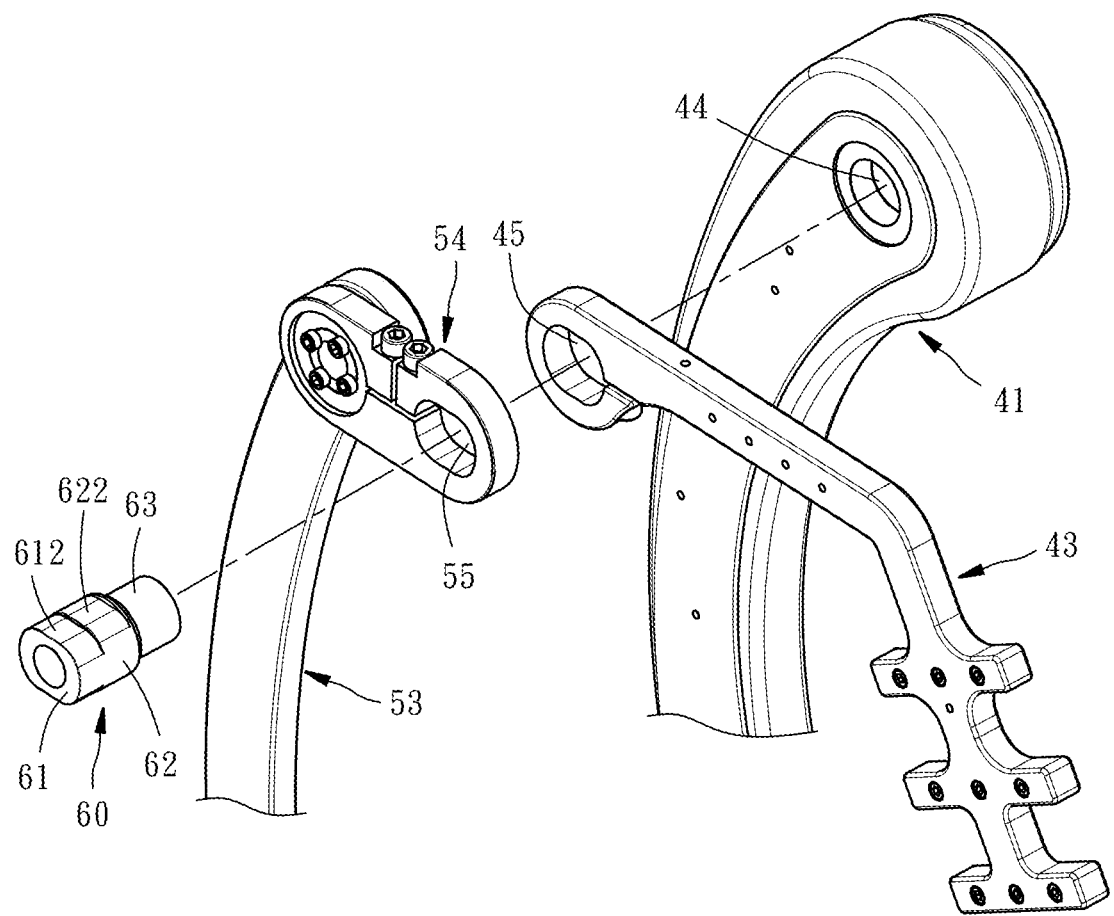
FIG. 4 is an exploded view of a part of the robotic arm in accordance with the first embodiment of the present invention.

The transmission linkage 40 comprises a first transmission link 41, a second transmission link 42 and a third transmission link 43. The first transmission link 41 has a bottom end thereof connected to a drive shaft (not shown) of the first driving source 31 by, for example, a coupling (not shown), such that the first transmission link 41 can be driven by the first driving source 31 to turn around a first axis A1. The second transmission link 42 has a front end thereof connected to a drive shaft (not shown) of the second driving source 32 by, for example, a coupling (not shown), such that the second transmission link 42 can be driven by the second driving source 32 to turn around a second axis A2 that is disposed in parallel to the first axis A1. The third transmission link 43 is adapted for the assembly of a multi-axis motion module 14 (as shown in FIG. 1), having a rear end thereof pivotally connected to an opposing top end of the first transmission link 41 by a pivot axle 60. More specifically, as shown in FIG. 4, the top end of the first transmission link 41 has a circular pivot hole 44; the third transmission link 43 has a non-circular first through hole 45 at the rear end thereof; the pivot axle 60 comprises a first non-circular section 61, a second non-circular section 62 connected to the first non-circular section 61, and a circular section 63 connected to the second non-circular section 62. The second non-circular section 62 of the pivot axle 60 is engaged in the non-circular first through hole 45 of the third transmission link 43. The circular section 63 of the pivot axle 60 is rotatably mounted in the circular pivot hole 44 of the first transmission link 41. Thus, the first transmission link 41 the third transmission link 43 can be biased relative to each other. Further, in this embodiment, the first non-circular section 61 of the pivot axle 60 defines two opposing first planes 612 that are disposed in parallel; the second non-circular section 62 defines two opposing second planes 622 that are disposed in parallel.

Figure 5:
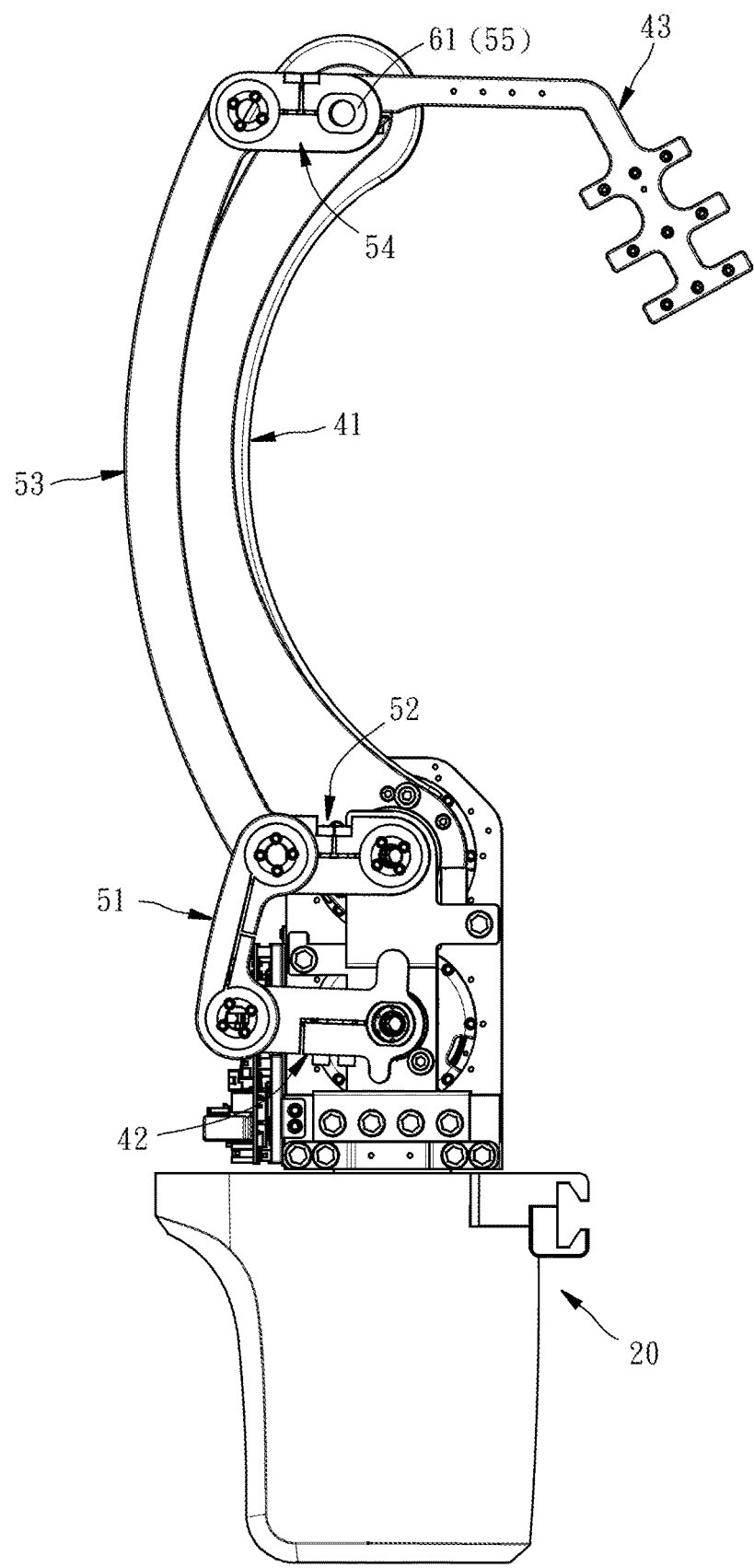
FIG. 5 is a plain view of the robotic arm in accordance with the first embodiment of the present invention.

Referring to FIG. 5 and FIG. 2 again, the driven link set 50 comprises a first driven link 51, a second driven link 52, a third driven link 53 and a fourth driven link 54. The first driven link 51 has a bottom end thereof pivotally connected to an opposing rear end of the second transmission link 42, and an opposing top end thereof pivotally connected to a rear end of the second driven link 52. The second driven link 52 has an opposing front end thereof pivotally connected to one side of the base frame 20 opposite to the drive module 30 such that the first driven link 51 can be driven by the second transmission link 42 to turn the second driven link 52 around the first axis A1. The third driven link 53 has a bottom end thereof pivotally connected to the top end of the first driven link 51 and the rear end of the second driven link 52, i.e., these three links are coaxially pivotally connected together. An opposing top end of the third driven link 53 is pivotally connected to a rear end of the fourth driven link 54. The fourth driven link 54 has an opposing front end thereof connected to the rear end of the third transmission link 43 by the pivot axle 60. More specifically, as shown in FIG. 4, the front end of the fourth driven link 54 has a non-circular second through hole 55. The non-circular second through hole 55 of the front end of the fourth driven link 54 is coupled to the first non-circular section 61 of the pivot axle 60 such that the fourth driven link 54 and the third transmission link 43 can be moved synchronously. As relationship between the fourth driven link 54 and the first transmission link 41, they can be biased relative to each other.

Figure 6:
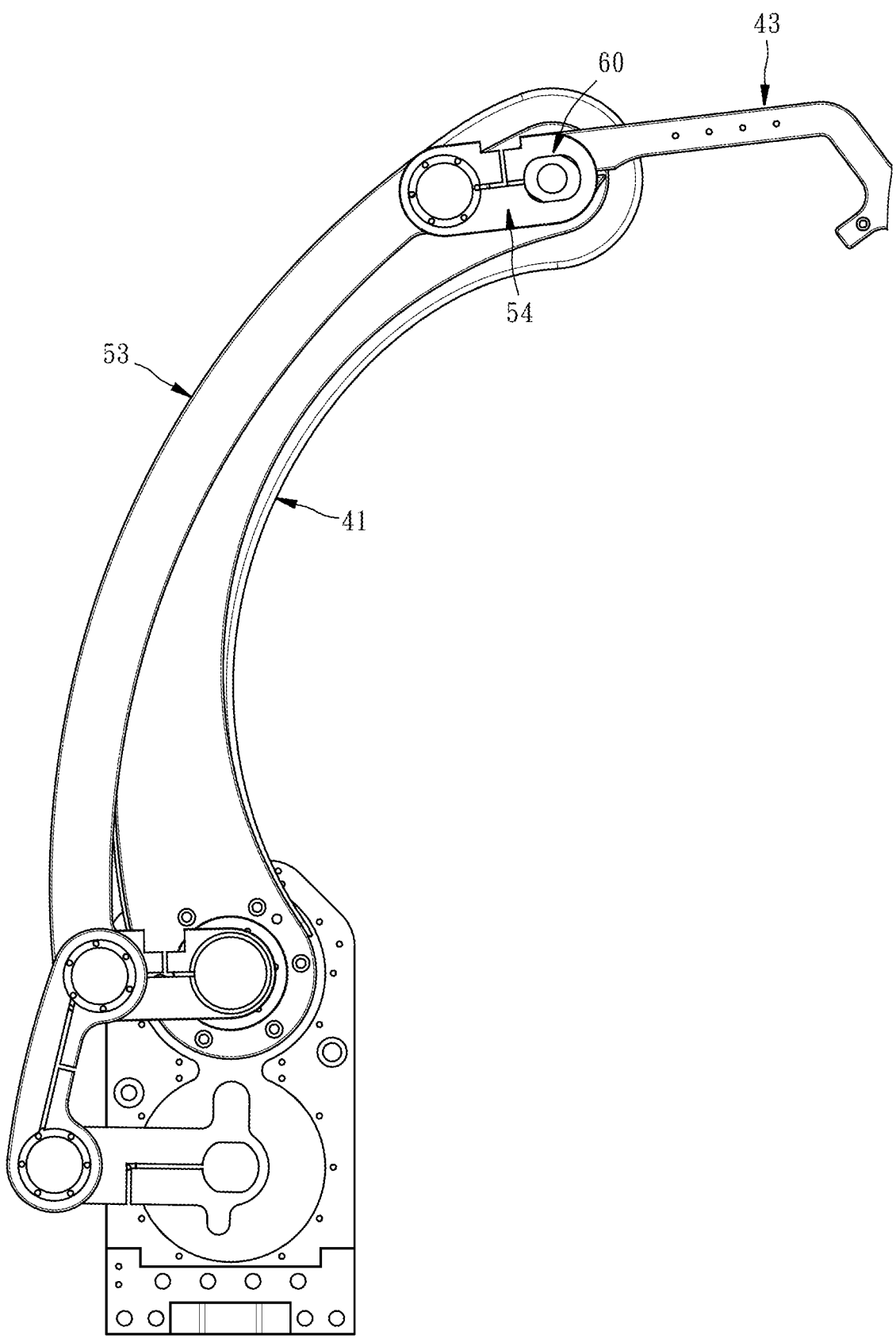
FIG. 6 is schematic operational view of the robotic arm in accordance with the first embodiment of the present invention, showing the front-rear position of the third transmission link adjusted.

As can be seen from the above, as shown in FIGS. 5 and 6, when the first transmission link 41 is driven by the first driving source 31 to turn around the first axis A1, the first transmission link 41 uses the pivot axle 60 to synchronize the third transmission link 43 and the fourth driven link 54, then the fourth driven link 54 will drive the top end of the third driven link 53, causing the third driven link 53 to pivot with its own bottom end. This allows the third transmission link 43 to be angled with the multi-axis motion module 14.

Figure 7:
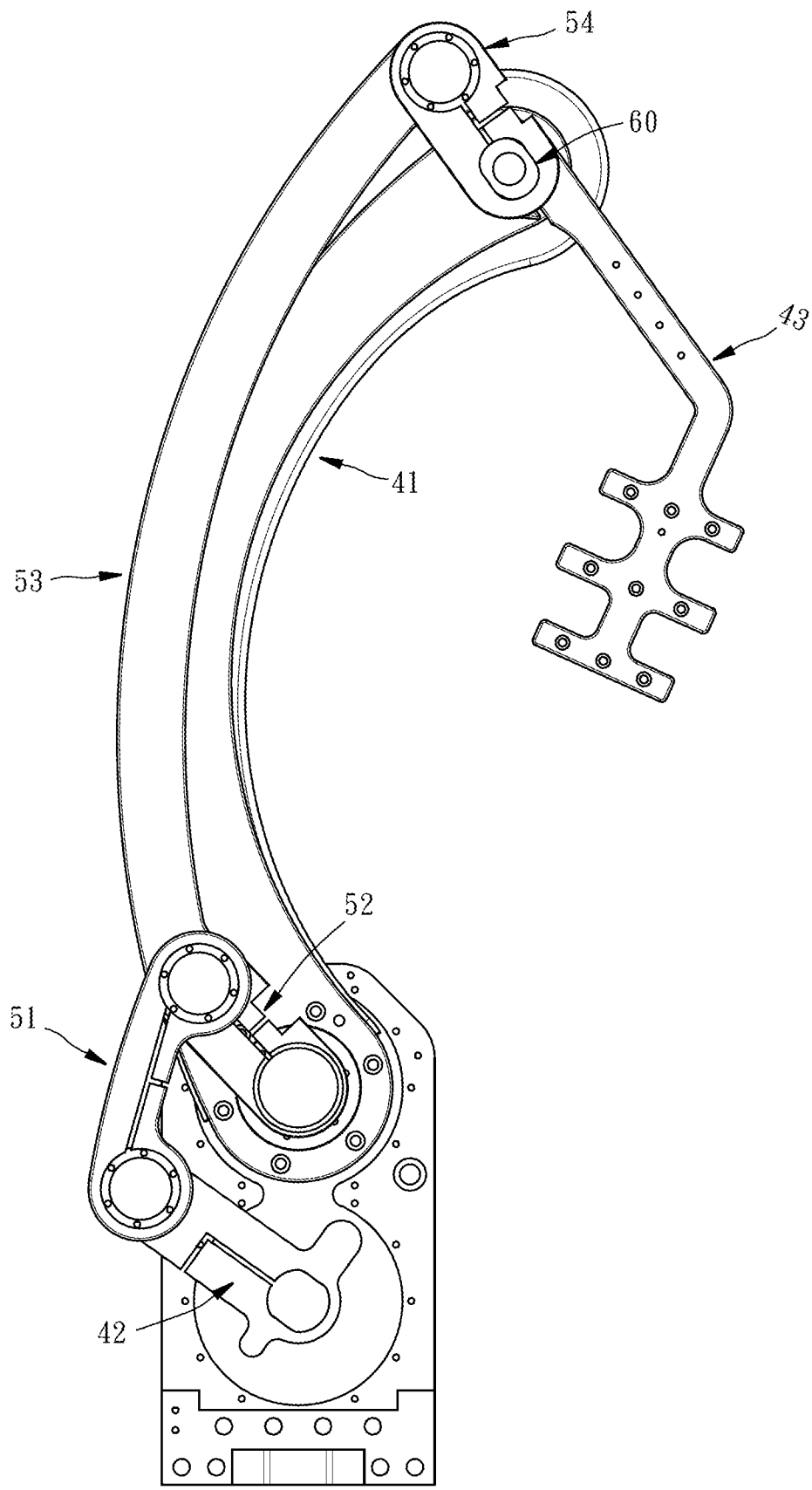
FIG. 7 is similar to FIG. 6, showing the angle of the third transmission link adjusted.

Referring to FIG. 7, when the second transmission link 42 is driven by the second driving source 32 to turn around the second axis A2, the second transmission link 42 drives the second driven link 52 to turn around the first axis A1, then the first driven link 51 and the second driven link 52 will drive the third driven link 53 to move up or down relative to the first transmission link 41. During vertical movement of the third drive link 53, the fourth driven link 54 is simultaneously driven to turn about the circular section 63 of the pivot axle 60. During pivoting of the fourth driven link 54, the second non-circular section 62 of the pivot axle 60 drives the third transmission link 43 to bias. This allows the third transmission link 43 to be angled with the multi-axis motion module 14.

On the other hand, as shown in FIG. 5, in the initial state, the second driven link 52 is parallel to the fourth driven link 54, the length of the second transmission link 42 is greater than the length of the second driven link 52, and the length of the second driven link 52 is equal to the length of the fourth driven link 54. The relationship of the second transmission link 42, the second driven link 52 and the fourth driven link 54 allows the range of motion of the third transmission link 43 to be amplified relative to the second transmission link 42 to meet the required working range.

Figure 8:
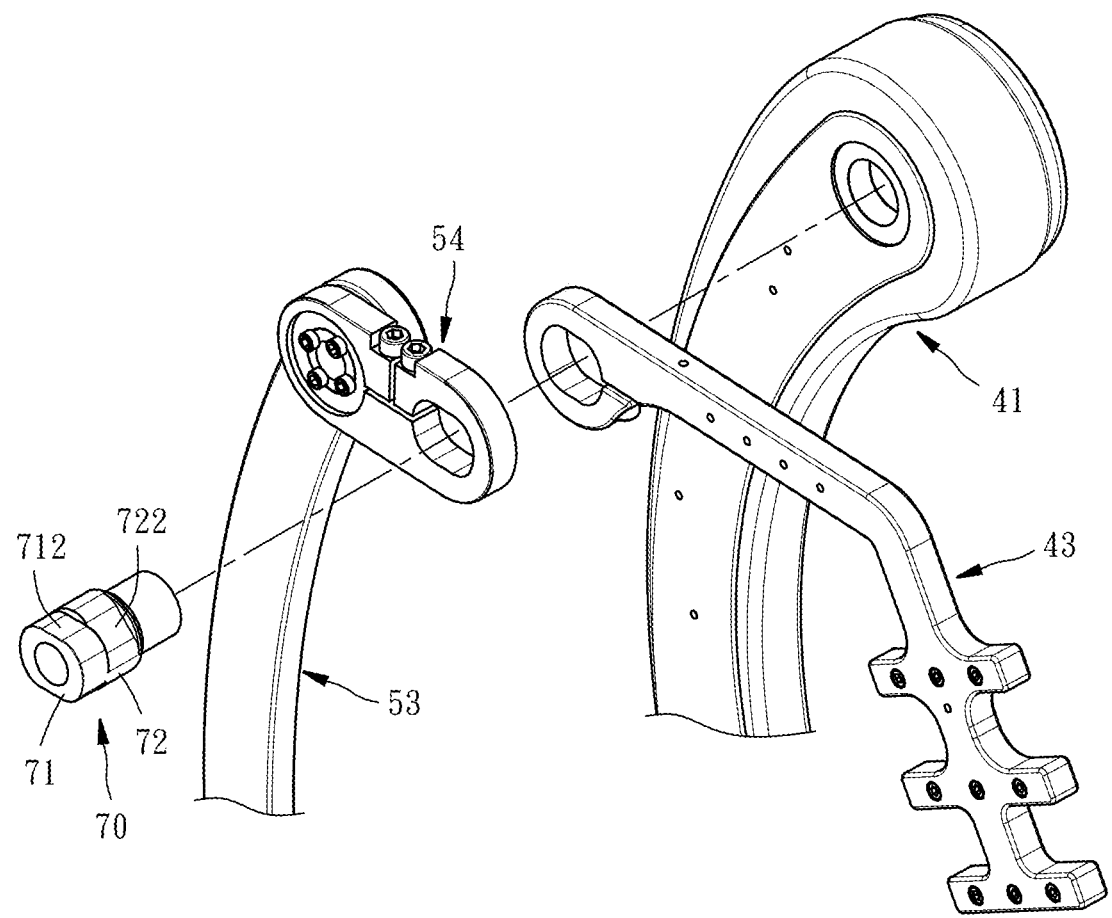
FIG. 8 is an exploded view of a part of a robotic arm in accordance with a second embodiment of the present invention.
Figure 9:
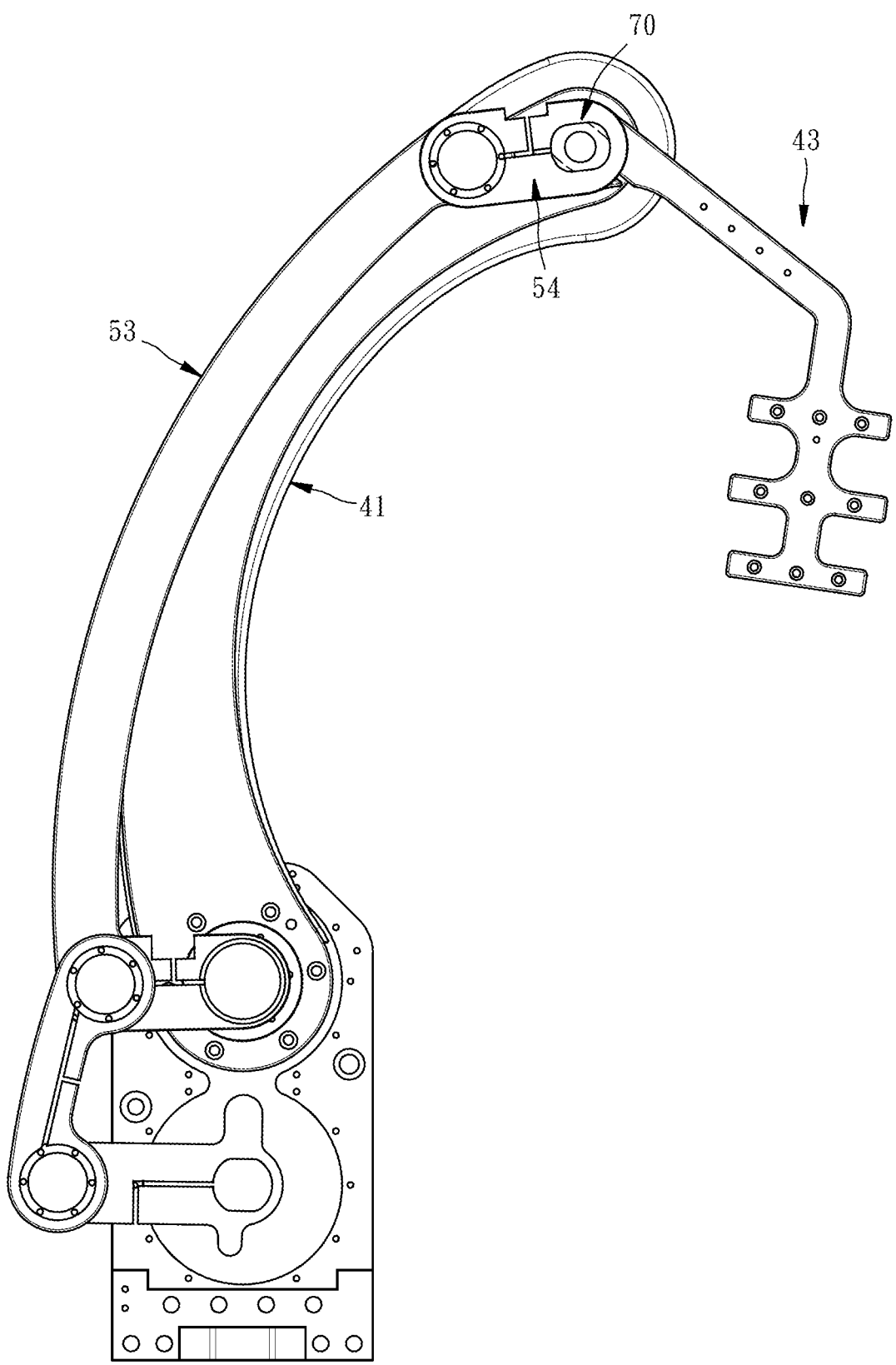
FIG. 9 is a plain view of the robotic arm in accordance with the second embodiment of the present invention.

Referring to FIGS. 8 and 9, in a second embodiment of the present invention, the first planes 712 of the first non-circular section 71 of the pivot axle 70 and the second planes 722 of the second non-circular section 72 of the pivot axle 70 are non-parallel to each other, defining therebetween a contained angle. Thus, after the first transmission link 41, the third transmission link 43, the third driven link 53 and the fourth driven link 54 are assembled by the pivot axle 70, the third transmission link 43 can make more changes in the working range by using the aforementioned contained angle to respond to different practical needs.

In conclusion, the robotic arm 10 of the present invention can perform multi-degree of freedom movement, so that the front-rear position and the deflection angle of the third transmission link 43 can be accurately adjusted according to actual needs, which is suitable for application in industrial/medical related fields. In addition, the robotic arm 10 of the present invention concentrates large-volume components (such as the first and second driving sources 31, 32) on the same side, thereby effectively achieving the purpose of volumetric compactness.

What is claimed is:
1. A robotic arm, comprising:
a base frame;
a drive module comprising a first driving source and a second driving source respectively mounted on said base frame;
a transmission linkage comprising a first transmission link, a second transmission link and a third transmis- sion link, said first transmission link is connected to said first driving source such that said first transmission link is driven by said first driving source to turn around a first axis; said second transmission link is connected to said second driving source such that said second transmission link is driven by said second driving source to turn around a second axis that is parallel to said first axis; said third transmission link is pivotally connected to said first transmission link; and a driven link set comprising a first driven link, a second driven link, a third driven link and a fourth driven link, said first driven link is pivotally connected to said second transmission link and said second driven link respectively; said second driven link is pivotally connected to said base frame, such that said first driven link is driven by said second transmission link to turn said second driven link around said first axis; said third driven link is pivotally connected to said first driven link and said second driven link coaxially, and is pivotally connected to said fourth driven link; said fourth driven link is connected to said third transmission link.

2. The robotic arm as claimed in claim 1, wherein said first driving source and said second driving source are located on said base frame at one same side.

3. The robotic arm as claimed in claim 1, wherein said second driven link is parallel to said fourth driven link; the length of said second transmission link is greater than the length of said second driven link; the length of said second driven link is equal to the length of said fourth driven link.

4. The robotic arm as claimed in claim 1, wherein said first transmission link, said third transmission link and said fourth driven link are connected by a pivot axle, said pivot axle comprising a first non-circular section, a second non-circular section connected to said first non-circular section, and a circular section connected to said second non-circular section, said first non-circular section being engaged with said fourth driven link, said second non-circular section being engaged with said third transmission link, said circular section being pivotally connected to said first transmission link.

5. The robotic arm as claimed in claim 4, wherein said first non-circular section of said pivot axle defines a first plane; said second non-circular section of said pivot axle defines a second plane, said second plane being parallel to said first plane.

6. The robotic arm as claimed in claim 4, wherein said first non-circular section of said pivot axle defines a first plane; said second non-circular section of said pivot axle defines a second plane, said second plane being non-parallel to said first plane.

* * * * *